United States Patent
Ali et al.

(10) Patent No.: US 11,833,132 B1
(45) Date of Patent: Dec. 5, 2023

(54) METHOD OF SYNTHESIS OF A NANOCOMPOSITE INCLUDING SILYMARIN-LOADED COLLAGEN NANOPARTICLES

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Ahmed Mohammed Abu-Dief Mohammed, Al-Ahsa (SA); Hazem Mohamed Shaheen, Al-Ahsa (SA); Gaber Elsaber Abd El-Wanis Batiha, Al-Ahsa (SA); Manal Aly Shalaby, Al-Ahsa (SA); Amany Mabrouk Abd Elhady Alamh, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/214,021

(22) Filed: Jun. 26, 2023

(51) Int. Cl.
*A61K 31/357* (2006.01)
*A61K 9/51* (2006.01)
*A61K 9/50* (2006.01)

(52) U.S. Cl.
CPC .......... *A61K 31/357* (2013.01); *A61K 9/5089* (2013.01); *A61K 9/5123* (2013.01); *A61K 9/5169* (2013.01)

(58) Field of Classification Search
None
See application file for complete search history.

(56) References Cited

FOREIGN PATENT DOCUMENTS

JP   6647925 B2   2/2020

OTHER PUBLICATIONS

Pankaj Rathore et al. "Collagen Nanoparticle-Mediated Brain Silymarin Delivery: An Approach for Treating Cerebral Ischemia and Reperfusion-Induced." Frontiers in Neuroscience, vol. 14, Oct. 2020, Article 538404, pp. 1-22. (Year: 2020).*
Jeong Eun Song, Yoo Shin Jeon, Jingwen Tian, Won Kyung Kim, Min Jung Choi, Cristiano Carlomagno, and Gilson Khang "Evaluation of silymarin/duck's feet-derived collagen/hydroxyapatite sponges for bone tissue regeneration." Materials Science and Engineering C, vol. 97, 2019, pp. 347-355. (Year: 2019).*
Rathore, et al.; "Collagen nanoparticle-mediated brain silymarin delivery: an approach for treating cerebral ischemia and reperfusion-induced brain injury." Frontiers in neuroscience 14 (2020): 538404.

(Continued)

*Primary Examiner* — Isaac Shomer
(74) *Attorney, Agent, or Firm* — Nath, Goldberg & Meyer; Richard C. Litman

(57) ABSTRACT

A method of synthesizing silymarin-loaded collagen collagen nanoparticles can include dissolving silymarin in an alcohol to provide a solution, mixing the solution with acetic acid to provide an acetic acid mixture, and adding the glutaraldehyde to the mixture to provide silymarin nanoparticles. The silymarin nanoparticles can be dissolved in a further alcohol and mixed for a period of time to provide a silymarin nanoparticle mixture. Then, the silymarin nanoparticles can be mixed with collagen nanoparticles to provide a silymarin/collagen mixture. Glutaraldehyde can be added to the collagen mixture to provide the nanocomposite formulation.

12 Claims, 2 Drawing Sheets

(56) References Cited

OTHER PUBLICATIONS

Arun, et al.; "Collagen nanoparticles in drug delivery systems and tissue engineering." Applied Sciences 11.23 (2021): 11369.

Awad, et al.; Cytotoxicity Effect Assessment of Theophylline Loaded with Collagen Nanoparticles., Damanhour Journal of Veterinary Sciences, 8 (2) (2022).

* cited by examiner

METHOD OF SYNTHESIS OF A NANOCOMPOSITE INCLUDING SILYMARIN-LOADED COLLAGEN NANOPARTICLES

BACKGROUND

1. Field

The disclosure of the present patent application relates to nanocomposite synthesis, and particularly, to a method of synthesizing silymarin-loaded collagen collagen nanoparticles.

2. Description of the Related Art

Alzheimer's disease (AD), the most common cause of dementia in older individuals, is a debilitating neurodegenerative disease for which there is currently no cure. It destroys neurons in parts of the brain, chiefly the hippocampus, which is a region involved in coding memories. Alzheimer's disease gives rise to an irreversible progressive loss of cognitive functions and of functional autonomy. The earliest signs of AD may be mistaken for simple forgetfulness, but in those who are eventually diagnosed with the disease, these initial signs inexorably progress to more severe symptoms of mental deterioration. While the time it takes for AD to develop will vary from person to person, advanced signs include severe memory impairment, confusion, language disturbances, personality and behavior changes, and impaired judgement. Persons with AD may become non-communicative and hostile. As the disease ends its course in profound dementia, patients are unable to care for themselves and often require institutionalization or professional care in the home setting. While some patients may live for years after being diagnosed with AD, the average life expectancy after diagnosis is eight years.

While many candidates are being developed, to-date no drugs have been developed that effectively treat or prevent Alzheimer's disease.

Thus, a method for treating or preventing Alzheimer's disease solving the aforementioned problems are desired.

SUMMARY

The present subject matter relates to a method of synthesizing a nanocomposite including silymarin-loaded collagen nanoparticles. The method can include dissolving silymarin in an alcohol to provide a solution, mixing the solution with acetic acid to provide an acetic acid mixture, and adding the glutaraldehyde to the mixture to provide silymarin nanoparticles. The silymarin nanoparticles can be dissolved in an alcohol and mixed for a period of time to provide a silymarin nanoparticle mixture. Then, the silymarin nanoparticles can be mixed with collagen nanoparticles to provide a silymarin/collagen mixture. Glutaraldehyde can be added to the collagen mixture to provide the nanocomposite formulation. As described herein, the nanocomposite formulation can effectively treat and prevent Alzheimer's disease (AD) in a subject in need thereof at very low effective doses.

In an embodiment, the present subject matter relates to a method of synthesizing a nanocomposite including silymarin-loaded collagen nanoparticles including extracting collagen from a marine source, mixing the collagen with an alcohol to provide collagen nanoparticles, dissolving silymarin in an alcohol to provide a solution, mixing the solution with acetic acid to provide an acetic acid mixture, adding glutaraldehyde to the mixture to provide silymarin nanoparticles, adding the silymarin nanoparticles to an alcohol to provide a silymarin nanoparticle mixture, adding the collagen nanoparticles to the silymarin nanoparticle mixture to provide a silymarin/collagen nanoparticle mixture, and adding glutaraldehyde to the silymarin/collagen mixture to provide the nanocomposite formulation.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
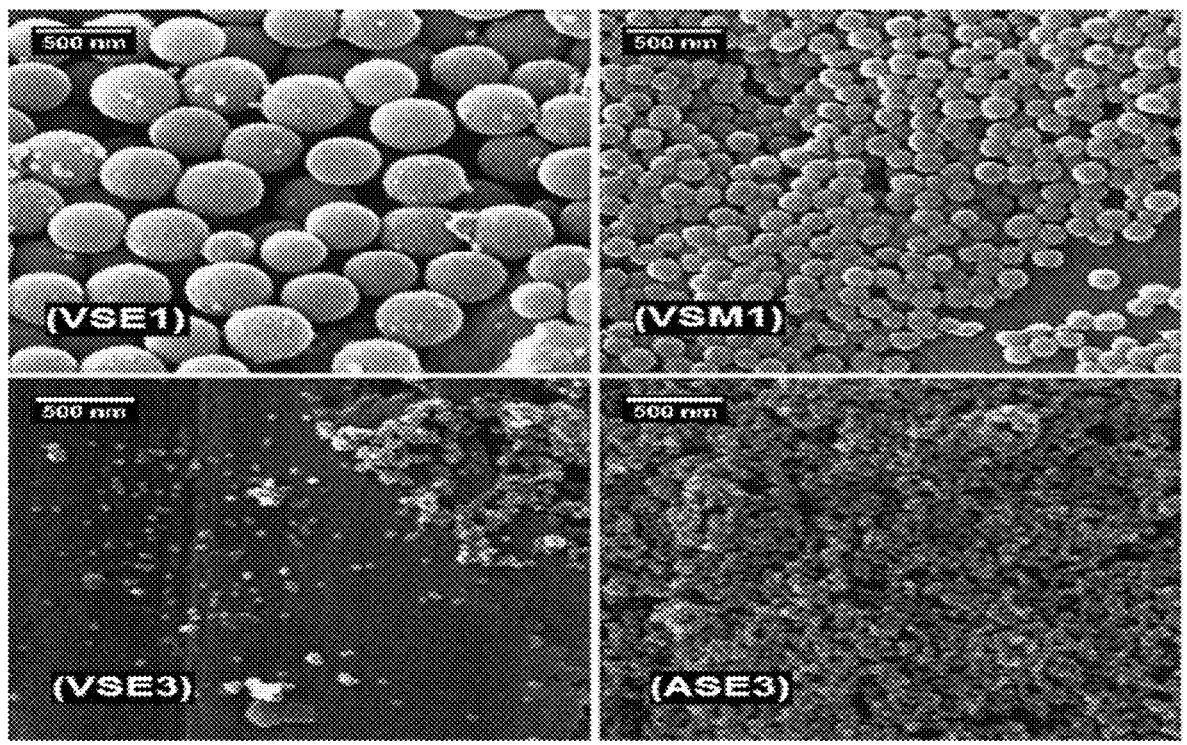
FIG. 1 depicts four scanning electron microscopy (SEM) images of the nanocomposite formulation.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

A "subject" herein is typically a human. In certain embodiments, a subject is a non-human mammal. Exemplary non-human mammals include laboratory, domestic, pet, sport, and stock animals, e.g., mice, cats, dogs, horses, and cows. As used herein, the term "patient" refers to any single subject for which treatment is desired. In certain embodiments, the patient herein is a human. A subject can be considered to be in need of treatment.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

In an embodiment, the present subject matter relates to a method of synthesizing a nanocomposite including silymarin-loaded collagen nanoparticles. The method can include dissolving silymarin in an alcohol to provide a solution, mixing the solution with acetic acid to provide an acetic acid mixture, and adding the glutaraldehyde to the mixture to provide silymarin nanoparticles. The silymarin nanoparticles can be dissolved in a further alcohol and mixed for a period of time to provide a silymarin nanoparticle mixture. Then, the silymarin nanoparticles can be mixed with collagen nanoparticles to provide a silymarin/collagen mixture. Glutaraldehyde can be added to the collagen mixture to provide the nanocomposite formulation. As described herein, the nanocomposite formulation can effectively treat and prevent Alzheimer's disease (AD) in a subject in need thereof at very low effective doses. In an embodiment, either or both of the alcohols used to dissolve the silymarin and the silymarin nanoparticles can be ethanol.

Silymarin has always been valued by researchers for its good efficacy and safety in treating liver disease. Recent studies have shown that silymarin also has good pharmacological activity in the nervous system, especially for the treatment of Alzheimer's disease.

Silymarin can control the production of Aβ by inhibiting the precursor substance of Aβ (β-amyloid precursor protein), and it can inhibit the polymerization of Aβ. Silymarin can also increase the acetylcholine content in the nervous system by inhibiting cholinesterase activity. At the same time, silymarin has the effect of resisting oxidative stress and the inflammatory response of the nervous system. These pharmacological activities contribute to the inhibition of the onset of AD.

As described herein, encapsulation of silymarin into collagen nanoparticles or the nanocomposite formulation, as described herein, can improve the therapeutic efficacy of silymarin by enhancing its bioavailability. As set forth herein, the nanocomposite formulation can reduce hippocampal tissue injury of $AlCl_3$-kindled rats due to its antioxidant and anti-inflammatory properties. In an embodiment, the nanocomposite formulation can reduce symptoms of Alzheimer's disease (AD).

Surface-modification, e.g., modification of surface charge and hydrophobicity, of the nanocomposite formulation can further enhance drug delivery to the brain through the bloodstream. Modification of the surface of the spheres facilitates identification of particular surface receptors of the cell and facilitates transcytosis.

According to an embodiment, collagen nanoparticles can be prepared by extracting collagen from a marine source and mixing the collagen with an alcohol. In an embodiment, the collagen can be extracted from the scales of mullet fish. In an embodiment, the alcohol can be ethanol. Then, the silymarin nanoparticles can be mixed with collagen nanoparticles to provide a silymarin/collagen mixture. Glutaraldehyde can be added to the collagen mixture to provide the nanocomposite formulation.

In an embodiment, the nanocomposite can have an average particle size ranging from about 30 nm to about 50 nm, or about 48 nm. In other embodiments, the nanocomposite can have an average particle size of 33 nm, 36 nm, 40 nm, 43 nm, 46 nm, or 49 nm.

An embodiment of the present subject matter is directed to a pharmaceutical composition comprising the nanocomposite formulation and a pharmaceutically acceptable carrier.

An embodiment of the present subject matter is directed to a method of making a pharmaceutical composition including mixing the nanocomposite formulation with a pharmaceutically acceptable carrier. For example, the method of making a pharmaceutical composition can include mixing the nanocomposite formulation under sterile conditions with a pharmaceutically acceptable carrier with preservatives, buffers, and/or propellants to create the pharmaceutical composition.

To prepare the pharmaceutical composition, the nanocomposite formulation, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The nanocomposite formulation can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the nanocomposite formulation or an amount effective to treat a disease, such as Alzheimer's disease (AD), may be determined initially from the Examples described herein and adjusted for specific targeted diseases using routine methods.

The nanocomposite formulation can be administered to a subject in need thereof. In an embodiment, the nanocomposite formulation can be administered to a subject in need thereof to treat Alzheimer's disease (AD).

An embodiment of the present subject matter is directed to a method of treating and preventing Alzheimer's disease (AD) in a subject, comprising administering to a subject in need thereof a therapeutically effective amount of the pharmaceutical composition according to the present subject matter.

The nanocomposite formulation or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

Synthesis of Silymarin Nanoparticles 500 mg of silymarin was dissolved in ethanol (50 ml) and put on a stirrer at a temperature of 100° C. for one hour. Then, acetic acid (100 ml/0.5 molar) was added slowly to the solution for one hour. This was followed by the addition of 2 ml glutaraldehyde, stirring the resulting solution overnight, and off-lining for ppt to form the silymarin nanoparticles.

Example 2

Preparation of Silymarin+Collagen Nanocomposite formulation

Scales of grey mullet fish were isolated by hand and cleared with distilled water. The samples were dried, placed in polybags, and kept at 25° C. until use. Collagen was isolated following the method of Shalaby et al. 2020 with minor adjustments. Non-collagenous proteins and pigments were removed from the fish scales with 0.1 N NaOH for two days, then cleared with distilled water. The samples were then extracted for two days with an acetic acid concentration (0.50 M), then homogenized for 3 hours. The supernatants were removed, and the remaining solution was filtrated.

The nanoprecipitation technique was used to create collagen nanoparticles using a non-solvent (ethanol). Ethanol was added utilizing a burette with free flow under stirring, which resulted in protein denaturation, from stretched to coil conformational change. Then, the silymarin nanoparticles were mixed with collagen nanoparticles in a stirrer to combine completely for one hour. To induce particle crosslinking, glutaraldehyde was added with stirring. The resulting solution of drug-encapsulated nanoparticles was centrifuged, lyophilized, and stored for later use.

Example 3

Physicochemical Characterization

Figure 3:
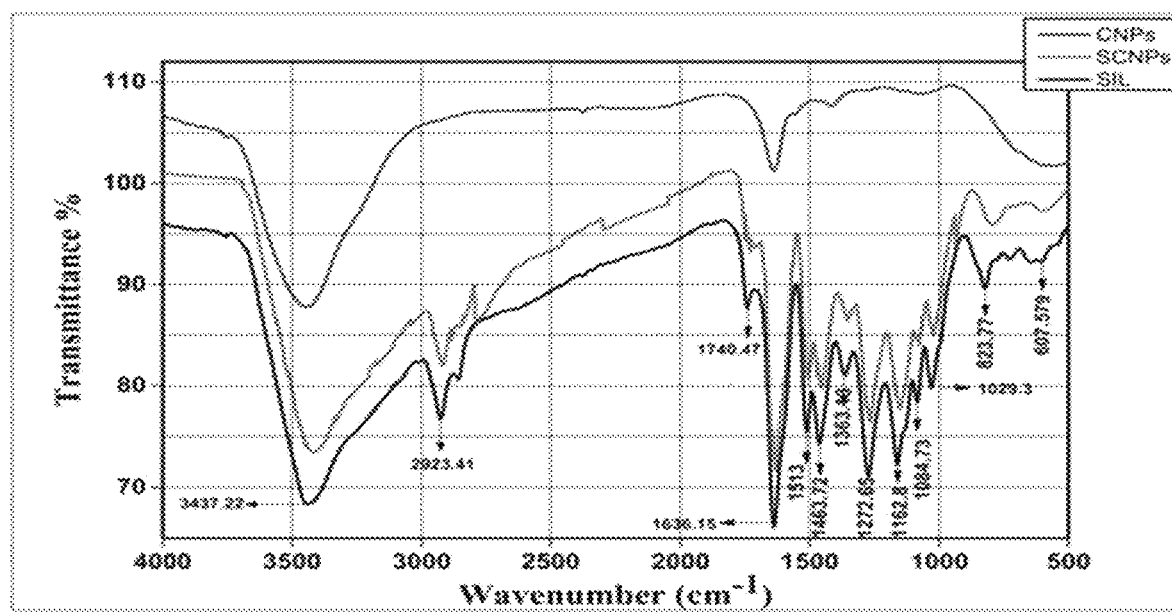
FIG. 3 depicts a Fourier Transform Infrared Spectroscopy (FTIR) spectrum for silymarin (SIL), collagen (CNPs), and the silymarin-collagen nanoparticles (SCNPs) or nanocomposite formulation.

The presence of nanoparticles was confirmed by scanning electron microscopy (See FIG. 1). FT-IR spectra were obtained by using an FT-IR spectrophotometer (Bruker Alpha Instrument). Using FT-IR spectra, functional groups present were detected and the presence of crosslinking in the collagen nanoparticles was determined after adding EDC-HCl and MDA. FT-IR spectrum was recorded in the frequency range of 4,000 to 400 $cm^{-1}$ (See FIG. 3).

Figure 2:
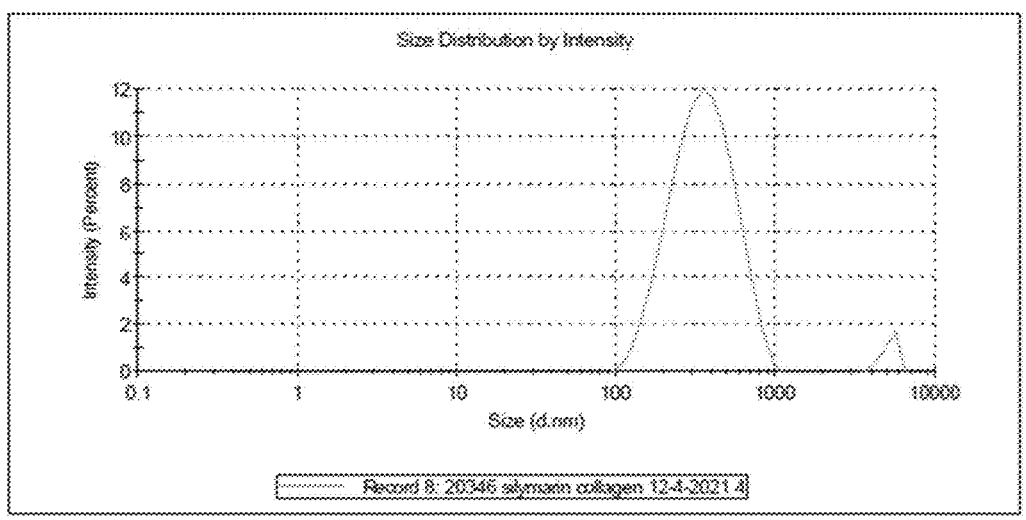
FIG. 2 depicts a graph showing size distribution by intensity of the nanocomposite formulation based on the Zeta-sizer test.

Particle size (PS) and polydispersity index (PDI) were determined using the dynamic light scattering (DLS) technique on a Zetasizer Nano ZS (Malvern Instruments Corp., Malvern, United Kingdom). All samples were diluted with Millipore-filtered deionized water to an appropriate scattering intensity. A Z-average diameter of the nanocomposite formulation was 346.5 nm (FIG. 2).

The nanocomposite formulation was morphologically examined using a technique called transmission electron microscopy (TEM) (TALOS Instrument, Thermo Fischer Scientific, United States) at AIIMS, New Delhi. Sample preparation involved putting a few drops of nanoparticles on a carbon-coated copper grid and negatively staining using 1% phosphotungstic acid (PTA). The excess stain solution was removed using filter paper followed by air drying. The next step included examination of stained films using a TEM instrument. (Data not shown)

Example 4

Evaluation of the Neuroprotective Effects of Silymarin (SM) on the Hippocampal Tissues of Aluminum Chloride ($AlCl_3$)-Induced Alzheimer-Like Disease in Rats The neuroprotective effects of silymarin (SM) were tested on the hippocampal tissues of aluminum chloride ($AlCl_3$)-induced Alzheimer's-like disease in rats using biochemical, histological, and immune-histochemical examination. For this experiment, 42 mature male albino rats were divided equally into 6 groups each of 7 rats as follows:

Group I: Rats injected with distilled water and served as the control group (non-induced);
Group II: Rats injected with $AlCl_3$;
Group III: Rats injected with $AlCl_3$, then silymarin;
Group IV: Rats injected with $AlCl_3$, then collagen;
Group V: Rats injected with $AlCl_3$ then silymarin nanoparticles;
Group VI: Rats injected with $AlCl_3$ then silymarin+collagen nanoparticles.

All of the experimental animals were sacrificed, and their brains dissected to take out the cortex section. The homogenates (10%, w/v) were then centrifuged at 10,000 rpm for 15 min and the supernatants were conserved at 80° C. for subsequent biochemical evaluations to determine, oxidative stress markers, catalase activity, superoxide dismutase, glutathione peroxidase, glutathione reductase; and lipid peroxidation.

Lipid peroxidation was determined by measuring the thiobarbituric reactive substances (TBARS) in the homogenate where:

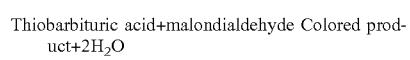

Thiobarbituric acid+malondialdehyde Colored product+$2H_2O$

Malondialdehyde (MDA), a major secondary product of lipid peroxidation (LPO) reacts with thiobarbituric acid (TBA), producing pink color adducts on heating. This reaction has been widely adopted as a sensitive method for lipid peroxidation that represents a major indicator of oxidative stress.

In four test tubes, homogenate supernatant (test) or water (blank) was added to 1 ml TCA and mixed well, then the solutions were centrifuged at 3000 rpm for 10 min. One milliliter of the supernatant of each of the previous four test tubes was added to 0.5 ml of TBA and heated for 30 min at 90° C. then cooled. The absorbance of samples (As) was read at 532 nm against blank.

The concentration of proteins was estimated. The levels of TBARS were calculated with the following equations:

For tissue homogenate:

$$As\text{:TBARS level (μmol/g protein)}=(0.156\times\text{total protein}\times1000)\times10, \text{where;}$$

As: absorbance of the sample (homogenate);
0.156: molar extinction coefficient (μM−1 cm$^{-1}$); and
10: the sample dilution factor.

Nitric oxide was rapidly oxidized to nitrite (NO$^{2-}$) and/or nitrate (NO$^{3-}$) by oxygen. In this method, nitrite was first treated with a diazotizing reagent, e.g., sulfanilamide (SA), in acidic media to form a transient diazonium salt. This intermediate was then allowed to react with a coupling reagent, N-naphthyl-ethylene diamine, to form a stable azo compound. The intense purple color of the product allows nitrite assay with high sensitivity and can be used to measure nitrite concentration as low as ~0.5 M level. The absorbance of this adduct at 540 nm is linearly proportional to the nitrite concentration in the sample.

The reagents included sulphanilamide (10 mM), N-(1-naphthyl) ethylenediamine, (1 mM), and standard sodium nitrite solution (100 μM). To four test tubes, each containing 1 ml sulphanilamide, 100 μl of either homogenate (test), standard solution (standard), or distilled water (blank) were added. The four test tubes were incubated for 5 minutes at room temperature. Then, 100 μl N-(1-naphthyl) ethylene diamine was added to all tubes and allowed to stand for 20 min at room temperature. The absorbance of the test and standard was read at 540 nm against blank.

The homogenate NO level was calculated according to the following equation:

$$\text{NO level (μM/g protein)}=[As\ Ast\times\text{Standard concentration}\times10]/\text{total proteins, where;}$$

As: Absorbance of the sample (homogenate);
Ast: Absorbance of standard; and
10: The sample dilution factor.

To determine homogenate reduced glutathione (GSH) level, GSH was allowed to react with 5,5'-dithio-bis-2-nitrobenzoic acid (DTNB) (equation below), known as Ellman's reagent, generating a yellow-colored 2-nitro-5-thiobenzoic acid product.

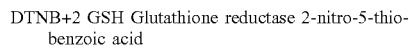

DTNB+2 GSH Glutathione reductase 2-nitro-5-thiobenzoic acid

The reagents used included sulfosalicylic acid, 4%; phosphate buffer, 0.1M, pH 7.4 and pH 8; DTNB, 10 mM, 19.8 mg in 10 ml phosphate buffer pH 8, and standard GSH, and 1 mg/dl (32.54 μM) in phosphate buffer pH 7.4.

Proteins in 0.1 ml of either homogenate supernatants (samples) were precipitated using 0.1 ml of 4% sulfosalicylic acid. The samples were kept at 4° C. for at least 1 hour and then subjected to centrifugation at 3000 rpm for 10 min at 4° C. The assay mixture contained ml supernatant, 2.7 ml phosphate buffer (0.1 M, pH 7.4), and 0.2 ml DTNB in a total volume of 3 ml.

The standard and blank experiment was carried out as above using 0.1 ml of standard GSH and distilled water, respectively instead of samples. The absorbance of the developed yellow color of samples and standard was read against blank at 412 nm.

The tissue contents of GSH were estimated using the following equation;

$$\text{GSH level (μmol/g protein)}=[As\ Ast\times\text{Standard concentration}\times10]/\text{total proteins,}$$

where;
As: Absorbance of the sample (homogenate);
Ast: Absorbance of standard; and
10: The tissue dilution.

Catalase reacts with a known quantity of $H_2O_2$. The reaction is stopped after exactly one minute with a catalase inhibitor. In the presence of peroxidase (HRP), remaining $H_2O_2$ reacts with 3,5-Dichloro-2-hydroxybenzene sulfonic acid (DHBS) and 4-aminophenazone (AAP) to form a chromophore with a color intensity inversely proportional to the amount of catalase in the original sample.

The reagents included:
buffer (Phosphate buffer, pH 7.0 Detergent)–100 mM/L;
$H_2O_2$ (substrate and standard) (Dilute 1000 times)–500 mM/L
Chromogen—Inhibitor—
Enzyme: Peroxidase 4-Aminoantipyrine Preservative→2000/L 2 mM/L.

Table 1 shows the results of the test.

TABLE 1

| Sample code | TBARS (μmol/g protein) | NO (μM/g protein) | GSH (μmol/g protein) | Catalase U/g |
|---|---|---|---|---|
| G1H1 | 0.73 | 33.33 | 13.40 | 60 |
| G1H3 | 0.69 | 36.11 | 14.51 | 65 |
| G2H1 | 1.54 | 61.67 | 12.06 | 54 |
| G2H3 | 1.48 | 65.00 | 14.51 | 65 |
| G3H1 | 0.50 | 30.00 | 14.96 | 67 |
| G3H4 | 0.64 | 36.11 | 14.51 | 65 |
| G4H1 | 0.74 | 37.22 | 24.78 | 111 |
| G4H3 | 0.60 | 36.11 | 11.61 | 52 |
| G5H4 | 1.23 | 61.67 | 24.78 | 111 |
| G5H2 | 0.58 | 28.89 | 26.12 | 117 |
| G6H1 | 0.82 | 37.22 | 14.96 | 67 |
| G6H3 | 0.87 | 35.00 | 14.07 | 63 |

Example 5

Evaluation of the Neuroprotective Effects Resulting from Pre-Treatment with the Nanocomposite Formulation Male albino rats were pretreated with one dose of the nano-formulation of 200 mg/kg/day for 15 days orally. The animals were then evaluated for neurobehavioral, infarct analysis, biochemical, histopathological studies. The animals treated with the nanocomposite formulation at this dose showed remarkable improvement in all parameters compared to the silymarin-treated group and other groups (Table 2).

TABLE 2

| Treatment | TBARS | NO | GSH | Catalase |
| --- | --- | --- | --- | --- |
| Control | 1.51 ± 0.02[a] | 62.44 ± 1.31[a] | 13.36 ± 0.71[c] | 59.67 ± 3.18[c] |
| AlCl$_3$ | 0.68 ± 0.04[bc] | 36.18 ± 0.58[bc] | 19.03 ± 3.89[bc] | 84.33 ± 17.27[bc] |
| Collagen | 0.71 ± 0.01[bc] | 34.91 ± 0.83[bc] | 14.44 ± 0.58[b] | 62.33 ± 1.45[b] |
| Silymarin | 0.58 ± 0.04[c] | 32.70 ± 1.80[c] | 14.69 ± 0.14[bc] | 65.33 ± 0.88[bc] |
| Sm-nano | 0.92 ± 0.19[bc] | 47.0 ± 9.62[bc] | 25.52 ± 0.39[bc] | 114.33 ± 1.76[bc] |
| Sm+ collagen | 0.85 ± 0.01[b] | 35.07 ± 1.22[b] | 14.64 ± 0.29[a] | 65.00 ± 1.15[a] |

It is to be understood that the method of synthesizing a nanocomposite including silymarin-loaded collagen nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing a nanocomposite including silymarin-loaded collagen nanoparticles, comprising:
   dissolving silymarin in a first alcohol to provide a solution;
   mixing the solution with acetic acid to provide an acetic acid mixture;
   adding glutaraldehyde to the mixture to provide silymarin nanoparticles;
   adding the silymarin nanoparticles to a second alcohol to provide a silymarin nanoparticle mixture;
   adding collagen nanoparticles to the silymarin nanoparticle mixture to provide a silymarin/collagen nanoparticle mixture;
   adding glutaraldehyde to the silymarin/collagen mixture to provide the nanocomposite formulation.

2. The method of claim 1, wherein the nanocomposite has an average particle diameter of about 30 nm to about 50 nm.

3. The method of claim 1, wherein the nanocomposite has an average particle diameter of about 48 nm.

4. The method of claim 1, wherein at least one of the first and the second alcohol are ethanol.

5. The method of claim 1, wherein the collagen nanoparticles are prepared by:
   extracting collagen from scales of mullet fish; and
   mixing the collagen with a third alcohol.

6. The method of claim 5, wherein the third alcohol is ethanol.

7. A method of synthesizing a nanocomposite including silymarin-loaded collagen nanoparticles, comprising:
   extracting collagen from a marine source;
   mixing the collagen with a first alcohol to provide collagen nanoparticles;
   dissolving silymarin in a second alcohol to provide a solution;
   mixing the solution with acetic acid to provide an acetic acid mixture;
   adding glutaraldehyde to the mixture to provide silymarin nanoparticles;
   adding the silymarin nanoparticles to a third alcohol to provide a silymarin nanoparticle mixture;
   adding the collagen nanoparticles to the silymarin nanoparticle mixture to provide a silymarin/collagen nanoparticle mixture;
   adding glutaraldehyde to the silymarin/collagen mixture to provide the nanocomposite formulation.

8. The method of claim 7, wherein the nanocomposite has an average particle diameter of about 30 nm to about 50 nm.

9. The method of claim 7, wherein the nanocomposite has an average particle diameter of about 48 nm.

10. The method of claim 7, wherein the marine source includes scales of mullet fish.

11. The method of claim 7, wherein at least one of the first alcohol, the second alcohol, and the third alcohol is ethanol.

12. The method of claim 11, wherein the first alcohol, the second alcohol, and the third alcohol are ethanol.

* * * * *

UNITED STATES PATENT AND TRADEMARK OFFICE
CERTIFICATE OF CORRECTION

PATENT NO.         : 11,833,132 B1
APPLICATION NO.    : 18/214021
DATED              : December 5, 2023
INVENTOR(S)        : Mai Mostafa Khalaf Ali et al.

Page 1 of 1

It is certified that error appears in the above-identified patent and that said Letters Patent is hereby corrected as shown below:

On the Title Page

In section Inventors (72), for Inventors 3-7, please delete and replace as follows:
Ahmed Mohammed Abu-Dief Mohammed, Al-Madina Al-Mounawara (SA); Hazem Mohamed Shaheen, Damanhour (EG); Gaber Elsaber Abd El-wanis Batiha, Damanhour (EG); Manal Aly Shalaby, Alexandria (EG); Amany Mabrouk Abd Elhady Alamh, Damanhour (EG).

Signed and Sealed this
Tenth Day of December, 2024

Katherine Kelly Vidal
*Director of the United States Patent and Trademark Office*